United States Patent [19]

Shishido

[11] Patent Number: 4,868,015

[45] Date of Patent: Sep. 19, 1989

[54] METHOD FOR MARKING ON AN INSERTABLE PORTION OF AN ENDOSCOPE

[75] Inventor: Yoshio Shishido, Sagamihara, Japan

[73] Assignee: Olympus Optical Co., Ltd., Japan

[21] Appl. No.: 191,705

[22] Filed: May 9, 1988

[30] Foreign Application Priority Data

May 9, 1987 [JP] Japan .............................. 62-113061

[51] Int. Cl.$^4$ ........................... B05D 5/00; B05D 3/02
[52] U.S. Cl. ..................................... 427/261; 427/286
[58] Field of Search ................... 427/256, 275, 2, 286, 427/261; 128/4, 6; 350/96.26

[56] References Cited

U.S. PATENT DOCUMENTS 3,625,731 12/1971 Taylor ................................. 427/256
3,691,001 9/1972 Takahashi et al. ............. 428/259 X

FOREIGN PATENT DOCUMENTS 57-22575 5/1982 Japan .
57-22884 5/1982 Japan .
59-79102 5/1984 Japan .
59-42002 12/1984 Japan .
60-128316 8/1985 Japan .

OTHER PUBLICATIONS

Gove, P. B. (editor), "Webster's Third New International Dictionary," Springfield, MA, Merriam-Webster Inc., 1986, pp. 1932, 2521, 2534.

Primary Examiner—Evan Lawrence
Attorney, Agent, or Firm—Ostrolenk, Faber, Gerb & Soffen

[57] ABSTRACT

A marking method for forming a mark on an outer surface of an insertable portion of an endoscope. The endoscope includes an outer cover having braided metal wires around which a fluorine-containing rubber is impregnated. A marking solution includes a urethane resin paint or an unvulcanized, fluorine-containing rubber (as a different color marking material) is dissolved in a ketone, ester or ether solvent which is applied to the outer surface and then baked or vulcanized at a temperature of 100° C. or higher, to produce a mark having strong adhesiveness.

16 Claims, 1 Drawing Sheet

METHOD FOR MARKING ON AN INSERTABLE PORTION OF AN ENDOSCOPE

BACKGROUND OF THE INVENTION

The present invention relates to a method for marking an insertable portion of an endoscope, and more particularly, a marking method for forming marks on an outside surface of an insertable portion of an endoscope.

As is well known, an endoscope may be used to observe the inside of a non-accessible area. For example, as shown in FIG. 2, when a foreign substance 15 is located within a duct 14 of a small diameter (decreasing the efficiency of duct 14), an insertable portion 12 of an industrial endoscope is inserted into the duct 14 to observe its inside. An objective optical system is provided on a distal end portion 13 of the endoscope to observe object 15. When any foreign substance such as substance 15 is found, an approximate range to the foreign substance 15 can be measured by knowing an inserted length 1 of the insertable portion 12. Thus, marks 16 (range scales) are provided over the whole length of the insertable portion 12.

Endoscopes for the use as described above are employed in numerous environments. Accordingly, an outer cover of the insertable portion of an endoscope must have a high chemical and mechanical durability. Similarly, marks 16 formed on the outer cover of the insertable portion must have a high durability so as not to fade due to chemical or mechanical action.

Conventionally, marks have been formed as disclosed in, for example, Japanese Patent Publication Sho No. 57-22575 and Japanese Utility Model Publication Sho No. 59-42002, in such a way that marks are drawn on the outer surface of an outer cover of the insertable portion of an endoscope with a marking material and are heated to deposit them thereon. In this case, the outer cover is made of ethylene tetrafluoride resin and the marking material is a synthetic ethylene fluoride resin having a lower melting point than that of the outer cover and includes a desired pigment.

However, the sheath tube of the insertable portion of an endoscope does not include the fine braided metal wire. Rather, the ethylene hexafluoride resin is merely applied to a ethylene tetrafluoride resin tube and baked at a temperature of 200° to 800° C. to deposit the marking material thereon. Marks on endoscopes produced according to this method do not have a high mechanical durability.

Furthermore, in the conventional marking method, as described above, the sheath tube comprising the insertable portion of the endoscope is made of ethylene tetrafluoride resin, and the marks are drawn on the outer surface of the outer sheath tube with ethylene tetrafluoride resin mixed with a pigment of a desired color. The tube with the markings thereon is baked at a temperature of 200° to 800° C. to adhere the markings to the tube.

However, problems of durability persist. The ethylene tetrafluoride resin is susceptible to being shaved off or damaged, particularly in industrial applications. Consequently, it is impossible to assure the durability of marks formed from ethylene hexafluoride resin on an endoscope surface.

In order to obtain a sufficient degree of mechanical durability, an outer sheath tube 17 for an endoscope is proposed in which fine metal wires 18 (such as stainless steel wires) are braided on a plane, as shown in FIG. 3.

In order to prevent release (flying out) of cut fine metal wires and to give hermetic sealing of an outer cover, an outer sheath tube 17 for an endoscope is developed which is formed by impregnating fluorine-containing rubber (fluorine elastomer) 19 between wires and then vulcanizing it. In order to provide marks 16 which are distinguishable, different colors are formed on the outer cover, however, adhesiveness of a marking material to the fine metal wires and the impregnated fluorine-contained rubber is required. In fact, even when a commonly used coating varnish is dissolved in a commonly used solvent and is applied to the outer cover, it has a poor adhesiveness and easily comes off in an environment of 20° C. which is common for an industrial endoscope.

SUMMARY OF THE INVENTION

It is an object of the present invention to provide a marking method for applying marks to the insertable portion of an endoscope which forms marks having a high degree of adhesiveness.

It is another object of the invention to provide a marking method whereby marks are formed on an endoscope and which have a high degree of mechanical durability to bending, friction, and the like in addition to good liquid-resisting qualities.

These and other objects are achieved by a method whereby marks are formed on an outer surface of the insertable portion of an endoscope by applying a solution thereon which dissolves a main marking material in a solvent of fluorine-containing unvulcanized rubber and baking the rubber to dry or vulcanize it.

According to the present invention, it is possible to form marks having good adhesiveness and mechanical durability to bending, friction, and the like in addition to good liquid-resisting qualities on the outer surface of an outer sheath tube of an endoscope.

DETAILED DESCRIPTION OF PREFERRED EMBODIMENTS

Figure 1:
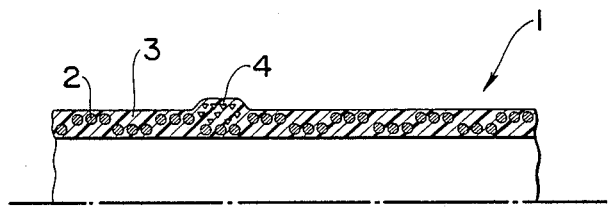
FIG. 1 is a cross-sectional view of the insertable portion of an endoscope having marks thereon formed by the marking method of the present invention.
Figure 2:
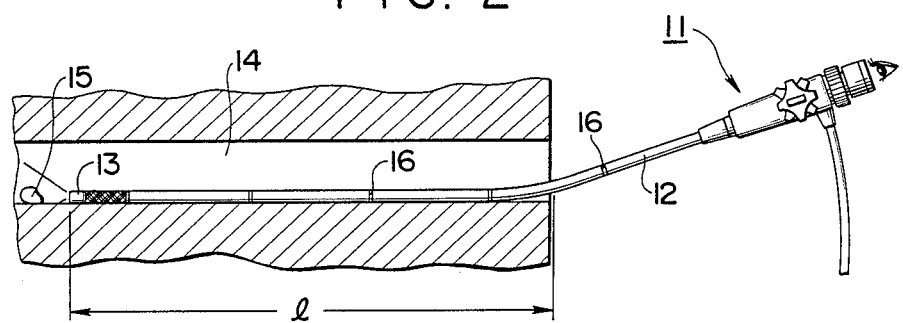
FIG. 2 is a schematic diagram of an example of an industrial endoscope in use; and, FIG. 3 is a schematic diagram of the insertable portion of an endoscope having marks thereon made by the marking method of the present invention.

Referring now to FIG. 1, an outer sheath tube 1, which forms an outer cover of the insertable portion of an endoscope, includes fine metal wires 2, fluorine-containing rubber 3 and marks 4.

Figure 3:
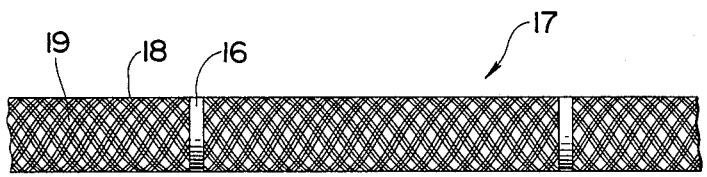

The fine metal wires 2 are formed into a pipe shape by braiding fine wires such as stainless steel in a plane, as shown in FIG. 3. The flourine-containing rubber 3 is placed in spaces between the fine metal wires 2. The outer sheath tube 1, as constructed above, has excellent mechanical durability. However, it is impossible to properly form marks on the outer surface thereof with a conventional method.

The present invention enable one to form marks having a good adhesiveness, mechanical durability and liquid resisting qualities on the outer surface of the tube 1 of the structure described above.

A first embodiment of a marking method for the outer sheath tube of the insertable portion of an endoscope according to the present invention will now be described.

A marking solution is prepared by mixing a urethane resin coating paint having good liquid-resisting qualities as a main solute with a ketone solvent for fluorine-containing unvulcanized rubber 3. When the marking solution is applied, it soaks an outer surface of the vulcanized, fluorine-containing rubber 3 and dissolves useless matters such as dirt, oils and fats which are attached to the fine stainless steel wires 2, allowing the marking solution to soak into the fluorine-containing rubber 3. Subsequently, a drying and baking operation is effected resulting in marks having good anchoring and fixing on the outer surface of the outer sheath tube.

The ketone solvent may be MEK (methyl ethyl ketone acetone, etc.). In addition to a ketone solvent the following types of solvents may be utilized: ester solvents (ethyl acetate, butyl acetate, etc); and ether solvents (ethyl ether, isopropyl ether, butyl ether, etc.)

As the fluorine-containing rubber, the following is preferred:

(1) Vinylidene fluoride-hexafluoropropylene rubber

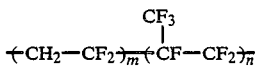

(A) Vinylidene fluoride/propylene hexafluoride copolymer
 Trade name: Viton
 Maker: Dupont Co. Ltd. (Showa Denko Co., Ltd.)
(B) Vinylidene fluoride/propylene pentafluoride copolymer
 Trade name: Techroflon Maker: Montefluos Co. (Nippon Zeon Co. Ltd.)
(C) Vinylidene fluoride/propylene trifluoride copolymer
 Trade name: Kellog
(2) Propylene-tetrafluoroethylene rubber

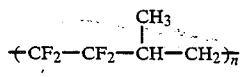

Ethylene tetrafluoride/propylene low-temperature emulsion copolymer
 Trade name: Aflas
 Maker: Asahi Glass Co., Ltd., Nippon Gosei Gomu Co., Ltd.
(3) Tetraflouroethylene-perfluoromethyl vinylether rubber (copolymer) (Copolymer of the ratio of 6:4)

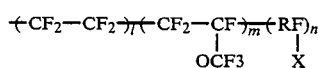

Trade name: Calrez
Maker: Dupont Co., Ltd.

For the urethane resin coating paint, a xylene solvent may be generally used. A ketone solvent may also be utilized in the present invention due to its dissolving property.

A second embodiment of the present invention will be described hereinafter.

In the second embodiment, a marking solution is prepared by dissolving a different color unvulcanized fluorine-containing rubber in ketone solvent. Alternatively, ester or ether solvent may be used. When marking solution is applied to fluorine-containing rubber 3 which has been vulcanized and an outer surface of the braided stainless steel fine wires 2, it slightly soaks into the vulcanized outer surface (which is a part of the impregnated fluorine-containing rubber) and is firmly fixed thereon.

Further, by way of heating and vulcanizing the applied material, it is possible to obtain marks 4 having excellent properties such as high liquid-resistance and mechanical durability to friction and bending, which are nearly equal to those of the outer cover.

A third embodiment of the present invention will be described hereinafter.

By blending a silane coupling agent (Shinetsu Chemical Co., Ltd.) (in a ratio of 1 to 3 wt %) into the marking solution described in the first and second embodiments, a stronger chemical coupling can be obtained to the outer cover, particularly to a metal surface. Consequently, it is possible to further improve the fixing quality to a composite material such as an object to be marked by the marking method of the present invention.

As the silane coupling agent, $\gamma$ methacryloxypropyl trimethoxysilane (trade name: KBM 530) and $\gamma$ mercaptopropyl trimethoxysilane (trade name: KBM 803), are especially effective.

As described above, the marking method of the present invention enables one to make marks with improved adhesiveness on both braided fine metal wires exposed on the outer cover of a sheath tube of an endoscope, and fluorine-containing rubber impregnated between the wires and exposed on the outer cover. To this end, urethane resin coating paint or unvulcanized fluorine-containing rubber which has a good liquid-resisting quality and mechanical durability is employeed as a marking material having a different color, and a ketone, ester or ether solvent is employed. After the marking solution is applied, a baking or vulcanizing operation is performed in a heating step at a temperature above 100° C., whereby the marks having increased adhesiveness are obtained.

The mixture ratio of the solute and solvent is about 1:4 (by weight).

Although the present invention has been described in connection with a preferred embodiment thereof, many other variations and modifications will now become apparent to those skilled in the art. It is preferred, therefore, that the present invention be limited not by the specific disclosure herein, but only by the appended claims.

What is claimed is:

1. A method for marking an insertable portion of an endoscope which portion includes an outer cover composed of braided metal wires impregnated with vulcanized, fluorine-containing rubber, the method comprising the steps of:
   preparing a solution by dissolving a main marking agent in a solvent for unvulcanized, fluorine-containing rubber;
   applying said solution on an outer surface of said insertable portion; and
   heating said surface on which said solution is applied to form marks.

2. A marking method according to claim 1, wherein said main marking agent includes a urethane resin coating paint.

3. A marking method according to claim 1, wherein said main marking agent includes an unvulcanized, fluorine-containing rubber having a different color than the outer cover.

4. A marking method according to claim 1, wherein said solvent is selected from the group consisting of a ketone solvent, an ester solvent and an ether solvent.

5. A marking method according to claim 1, wherein said marking solution comprises an unvulcanized rubber which is a different color than the outer cover of the endoscope and which is dissolved in a ketone or ester solvent.

6. A marking method according to claim 1, further comprising blending a silane coupling agent into said marking solution.

7. A marking method according to claim 6, wherein said silane coupling agent is selected from the group consisting of γ methacryloxy propyl trimethoxy silane and γ mercaptopropyl trimethoxy silane.

8. A marking method as claimed in claim 6, wherein the silane coupling agent is present in the marking solution in a range of about 1 to about 3 wt. %.

9. A marking method according to claim 1, wherein said main marking agent is dissolved in the solvent in a ratio of about 1 to about 4 by weight.

10. A marking method according to claim 1, wherein the unvulcanized, fluorine containing rubber is selected from the group consisting of vinylidene fluoride-hexafluoropropylene rubber, propylene-tetrafluoroethylene rubber and tetrafluoroethylene-perfluoromethyl vinylether rubber.

11. A marking method according to claim 10, wherein the fluorine containing rubber is vinylidene fluoride-hexafluoropropylene rubber.

12. A marking method according to claim 11, wherein the vinylidene fluoride-hexafluoropropylene rubber is selected from the group consisting of vinylidene fluoride/propylene hexafluoride copolymer, vinylidene fluoride/propylene pentafluoride copolymer and vinylidene fluoride/propylene trifluoride copolymer.

13. A marking method according to claim 10, wherein the fluorine containing rubber is propylene-tetrafluoroethylene rubber.

14. A marking method according to claim 13, wherein the propylene-tetrafluoroethylene rubber is an ethylene tetrafluoride/propylene low-temperature emulsion copolymer.

15. A marking method according to claim 10, wherein the fluorine containing rubber is tetrafluoroethylene-perfluoromethyl vinylether rubber.

16. A marking method according to claim 15, wherein the tetrafluoroethylene-perfluoromethyl vinylether rubber is a copolymer having a ratio 6 to 4.

* * * * *